(12) United States Patent
Priore

(10) Patent No.: US 8,993,964 B2
(45) Date of Patent: Mar. 31, 2015

(54) SYSTEM AND METHOD FOR DETECTING CONTAMINANTS IN A SAMPLE USING NEAR-INFRARED SPECTROSCOPY

(75) Inventor: Ryan Priore, Wexford, PA (US)

(73) Assignee: ChemImage Technologies LLC, Pittsburgh, PA (US)

( * ) Notice: Subject to any disclaimer, the term of this patent is extended or adjusted under 35 U.S.C. 154(b) by 1028 days.

(21) Appl. No.: 12/932,957

(22) Filed: Mar. 10, 2011

(65) Prior Publication Data

US 2012/0229796 A1 Sep. 13, 2012

Related U.S. Application Data

(60) Provisional application No. 61/311,814, filed on Mar. 9, 2010.

(51) Int. Cl.
*G01J 5/00* (2006.01)
*G01N 21/359* (2014.01)
*G01N 21/65* (2006.01)
*G01N 21/3563* (2014.01)

(52) U.S. Cl.
CPC .............. *G01N 21/359* (2013.01); *G01N 21/65* (2013.01); *G01N 21/3563* (2013.01)
USPC ...................................... 250/338.1

(58) Field of Classification Search
CPC .................................................. G01N 21/3577
USPC .......................... 250/338.1–338.5, 330–335, 250/336.1–336.2, 340, 341.1–341.8
See application file for complete search history.

(56) References Cited

U.S. PATENT DOCUMENTS

| 4,559,075 | A | | 12/1985 | Freepons |
| 5,187,368 | A | * | 2/1993 | Galante et al. ............. 250/341.5 |
| 6,587,575 | B1 | | 7/2003 | Windham |

(Continued)

FOREIGN PATENT DOCUMENTS

| WO | WO02063939 A2 | 8/2002 |
| WO | WO2009042466 A1 | 4/2009 |
| WO | WO2010053979 A2 | 5/2010 |

OTHER PUBLICATIONS

Singh et al., "Near-infrared hyperspectral imaging for quality analysis of agricultural and food products," 2010, SPIE Proceedings, vol. 7676, pp. 767603-1 to 767603-9.*

(Continued)

*Primary Examiner* — Kiho Kim
(74) *Attorney, Agent, or Firm* — Pepper Hamilton LLP

(57) ABSTRACT

A system and method for detecting a contaminant in a sample. The contaminant may comprise melamine or a derivative thereof and the sample may comprise a feed material. The method may comprise illuminating a sample to thereby generate a first plurality of interacted photons, collecting the interacted photons, passing the interacted photons through a tunable filter, and detecting the interacted photons to generate a near infrared data set representative of the sample. This near infrared sample may comprise a hyperspectral near infrared image. The method may further comprise fusing said near infrared data set with a Raman data set representative of sample. A system may comprise an illumination source, one or more collection optics, a tunable filter, and a detector configured to generate a near infrared data set. The system may further comprise a second detector configured for generating a Raman data set representative of a sample.

22 Claims, 6 Drawing Sheets
(1 of 6 Drawing Sheet(s) Filed in Color)

(56) References Cited

U.S. PATENT DOCUMENTS

| | | | |
|---|---|---|---|
| 6,950,184 B2 | 9/2005 | Stewart | |
| 7,428,045 B2 | 9/2008 | Stewart | |
| 8,054,454 B2* | 11/2011 | Treado et al. | 356/73 |
| 2003/0030800 A1 | 2/2003 | Golden | |
| 2004/0236229 A1* | 11/2004 | Freeman et al. | 600/474 |
| 2006/0055923 A1 | 3/2006 | Stewart | |
| 2009/0087033 A1 | 4/2009 | Chao | |
| 2009/0207046 A1* | 8/2009 | Arrighetti | 340/937 |
| 2011/0207231 A1* | 8/2011 | Natan et al. | 436/98 |

OTHER PUBLICATIONS

Liu et al., "Development of simple algorithms for the detection of fecal contaminants on apples from visible/near infrared hyperspectral reflectance imaging," 2007, Journal of Food Engineering, vol. 81, pp. 412-418.*

Kim et al, "Line-Scan Hyperspectral Imaging Platform for Agor-Food Safety and Quality Evaluation: System Enhancement and Characterization," American Society of Agricultural and Biological Engineers, vol. 54(2), p. 709-711, 2011.

Vision Systems Design, Hyperspectral Imaging System Sorts Seeds, Nov. 12, 2012.

Toray Industries, Inc., "Flame-Resistant Polamides," Japan Tokkyo Koko JP 8222348 Chem Abstracts (1982).

Schneider, J.R., et al., "Measurement and Calculation of the Infrared and Raman Active Molecular and Lattice Vibrations of the Crystalline Melamine (1,3,5-Triamino-S-Triazine)", J. of Molecular Structure (1975) 29:1-14.

Ozaki,Y., "Raman Spectroscopy in Spectral Methods in Food Analysis," (1999) 427-462, Marcel Dekker, New York, Ed. :M.M. Mossoba.

Tseng, C.H. et al., "FT-Raman Determination of Melamine and Melamine Cyanurate in Nylon", Applied Spectroscopy (1994) 48:4 535-537.

Scheepers, ML et al., "Investifation of Melamine-Formaldehyde Cure by Fourier Transform Raman Spectroscopy," Vibrational Spectroscopy (1993) 6:55-69.

Gowen. et al. "Hyperspectral imaging—Am Emerging Process Analytical Tool for Food Quality and Safety Control," Trends in Food Science & Technology 18 (2007) 590-598.

H.R. Morris et al., Appl. Spectrosc. 50, 805 (1996).

FDA Updates Health Information Advisory on Melamine Contamination, FDA, available from: http://www.fda.gov/NewsEvents/Newsroom/PressAnnouncements/2008/ucm116955.htm, accessed Jun. 28, 2011.

FDA Detects Melamine Contamination in Flavored Drink, FDA, Available from: http://www.fda.gov/NewsEvents/Newsroom/PressAnnouncements/2008/ucm116961.htm. (2007). Accessed Jun. 28, 2011.

D.R. Shelton et al., Appl. Environ. Microbiol. 63, 2832 (1997).

FSIS Testing Results for Melamine in Retail Meat and Poultry Products, USDA, http://www.fsis.usda.gov/PDF/Testing_Results_Melamine_May2009.pdf, last accessed Jun. 28, 2011.

J. R. Ferraro and K. Nakamoto, Introductory Raman Spectroscopy (Academic Press, San Diego, 1994).

Interim Melamine and Analogues Safety/Risk Assessment, FDA, Available from: http://www.fda.gov/Food/FoodSafety/FoodContaminantsAdulteration/ChemicalContaminants/Melamine/ucm164658.htm, Accessed Jun. 28, 2011.

Liu et al., Potential of Raman Spectroscopy and Imaging Methods for Rapid and Routine Screening of the Presence of Melamine in Animal Feed and Foods, Applied Spectroscopy, vol. 63, No. 4, 2009.

* cited by examiner

SYSTEM AND METHOD FOR DETECTING CONTAMINANTS IN A SAMPLE USING NEAR-INFRARED SPECTROSCOPY

CROSS-REFERENCE TO RELATED APPLICATION

This application claims benefit of and priority to U.S. Provisional Application Ser. No. 61/311,814 entitled "SYSTEM AND METHOD FOR DETECTING CONTAMINANTS IN A SAMPLE USING NEAR-INFRARED SPECTROSCOPY" and filed Mar. 9, 2010, the disclosure of which is incorporated by reference herein in its entirety.

BACKGROUND

Melamine is a common chemical recently found to have been added to animal feed in an attempt to increase the apparent protein content of the product. As a result, a substantial amount of the animal feed that entered the consumer market was contaminated, killing a large number of animals. Current methods of detecting melamine and other contaminants are labor-intensive and time consuming. There exists a need for rapid, non-destructive, specific, low-cost, and routine systems and methods for assessing feed samples for the presence or absence of melamine. Additionally, it would be helpful to be able to detect other contaminants such as cyanuric acid, ammeline, and ammelide, which may also be found in feed materials. These agents may be present in due to their individual addition to the feed or as a result of melamine degradation.

Fast melamine screening requires minimal sample preparation (e.g., no extraction/centrifugation), routine analysis of a number of samples without reagents, minimal procedures and ease of operation. Such systems and methods are increasingly important because of the potential public and animal health concerns. In addition, systems and methods are needed for melamine screening to prevent protein fraud.

Spectroscopic imaging combines digital imaging and molecular spectroscopy techniques, which can include Raman scattering, fluorescence, photoluminescence, ultraviolet, visible and infrared absorption spectroscopies. When applied to the chemical analysis of materials, spectroscopic imaging is commonly referred to as chemical imaging. Instruments for performing spectroscopic (i.e. chemical) imaging typically comprise an illumination source, image gathering optics, focal plane array imaging detectors and imaging spectrometers.

In general, the sample size determines the choice of image gathering optic. For example, a microscope is typically employed for the analysis of sub micron to millimeter spatial dimension samples. For larger objects, in the range of millimeter to meter dimensions, macro lens optics are appropriate. For samples located within relatively inaccessible environments, flexible fiberscope or rigid borescopes can be employed. For very large scale objects, such as planetary objects, telescopes are appropriate image gathering optics.

For detection of images formed by the various optical systems, two-dimensional, imaging focal plane array ("FPA") detectors are typically employed. The choice of FPA detector is governed by the spectroscopic technique employed to characterize the sample of interest. For example, silicon ("Si") charge-coupled device ("CCD") detectors or CMOS detectors are typically employed with visible wavelength fluorescence and Raman spectroscopic imaging systems, while indium gallium arsenide ("InGaAs") FPA detectors are typically employed with near-infrared spectroscopic imaging systems. For some modalities, intensified charge-coupled devices ("ICCD") may also be used.

Wide-field spectroscopic imaging of a sample can be implemented by collecting spectra over the entire area encompassing the sample simultaneously using an electronically tunable optical imaging filter such as an acousto-optic tunable filter ("AOTF") or a liquid crystal tunable filter ("LCTF"). Here, the organic material in such optical filters are actively aligned by applied voltages to produce the desired bandpass and transmission function. The spectra obtained for each pixel of such an image thereby forms a complex data set referred to as a hyperspectral image which contains the intensity values at numerous wavelengths or the wavelength dependence of each pixel element in this image.

Spectroscopic devices operate over a range of wavelengths due to the operation ranges of the detectors or tunable filters possible. This enables analysis in the Ultraviolet ("UV"), visible ("VIS"), near infrared ("NIR"), short-wave infrared ("SWIR"), mid infrared ("MIR") wavelengths, long wave infrared wavelengths ("LWIR"), and to some overlapping ranges. These correspond to wavelengths of approximately 180-380 nm ("UV"), 380-700 nm ("VIS"), 700-2500 nm ("NIR"), 850-1800 nm ("SWIR"), 650-1100 nm ("MWIR"), 400-1100 ("VIS-NIR") and 1200-2450 ("LWIR").

SUMMARY OF THE INVENTION

The present disclosure relates to a system and method for detecting contaminants in a sample. More specifically, the present disclosure relates to a system and method for detecting contaminants using near infrared spectroscopy and near infrared hyperspectral imaging. The present disclosure also relates to a system and method for fusing different types of data, such as near infrared and Raman, to increase accuracy and reliability of sample assessment. The systems and methods of the present disclosure overcome the limitations of the prior art and provide for the rapid, accurate, non-destructive, specific, and routine screening of the presence of melamine and other contaminants in food and feed. This assessment holds potential for ensuring public and animal safety and security.

BRIEF DESCRIPTION OF THE DRAWINGS

The accompanying drawings, which are included to provide further understanding of the disclosure and are incorporated in and constitute a part of this specification, illustrate embodiments of the disclosure and, together with the description, serve to explain the principles of the disclosure. The patent or application file contains at least one drawing executed in color. Copies of this patent or patent application publication with color drawing(s) will be provided by the Office upon request and payment of the necessary fee.

DETAILED DESCRIPTION

Reference will now be made in detail to the embodiments of the present disclosure, examples of which are illustrated in the accompanying drawings. Wherever possible, the same reference numbers will be used throughout to refer to the same or like parts.

The present disclosure provides for a system and method for detecting the presence of a contaminant in a sample. In one embodiment, near infrared ("NIR") spectroscopic techniques may be used to detect contaminants in a sample and to determine their concentrations. NIR spectroscopy is a non-contact, non-destructive analytical characterization tool that may be applied to assess a broad range of materials. The NIR region of the electromagnetic spectrum encompasses radiation with wavelengths of 0.78 to 2.5 μm (12,800 to 4,000 cm$^{-1}$). NIR spectra result from the overtone and combination bands of fundamental mid-infrared (MIR) bands. Among the many desirable characteristics, NIR is used to rapidly obtain both qualitative and quantitative information about the molecular makeup of a material. Digital imaging, on the other hand, provides a means to obtain optical (i.e., spatial—morphological, topographical, etc.) information about a material. By combining the spatial information obtained from digital imagery and the spectral information obtained from NIR spectroscopy, the chemical makeup of complex material matrices can be mapped out in both two and three spatial dimensions. NIR chemical imaging combines NIR spectroscopy and digital imaging for the molecular-specific analysis of materials.

Figure 1:
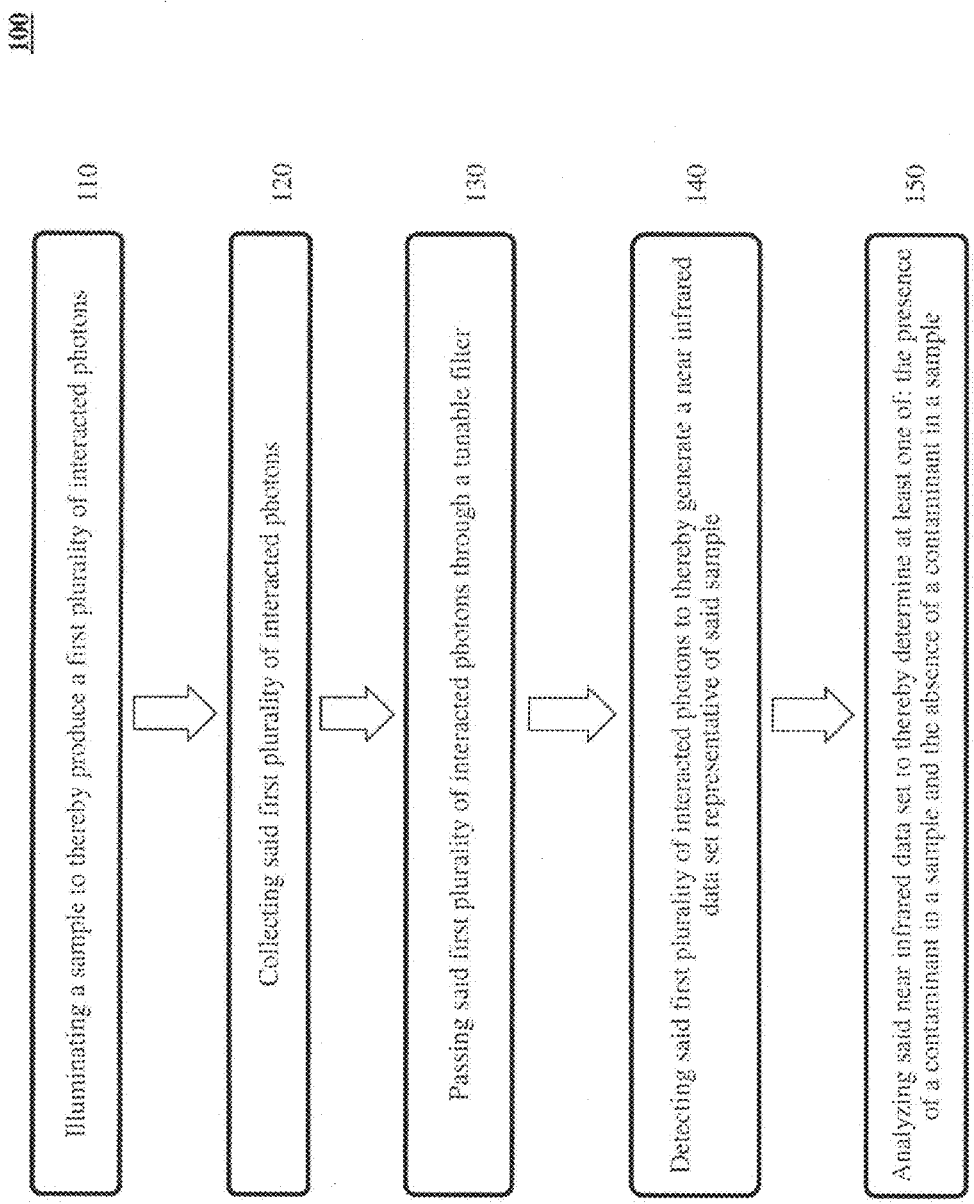
FIG. 1 is illustrative of one embodiment of a method of the present disclosure.

In one embodiment, illustrated by FIG. 1, the present disclosure provides for a method 100. The method 100 may comprise illuminating a sample to thereby generate a first plurality of interacted photons in step 110. In one embodiment, the sample may comprise a food and/or feed material. This material may comprise wheat flour, corn, gluten, soybean meal, and combinations thereof. These interacted photons may comprise photons scattered by the sample, photons emitted by the sample, photons reflected by the sample, photons absorbed by the sample, and combinations thereof. These interacted photons may be collected in step 120. This collection may be accomplished using one or more collection optics. In step 130 these interacted photons may be passed through a tunable filter. In one embodiment, this tunable filter may comprise a multi-conjugate liquid crystal tunable filter, a liquid crystal tunable filter, and combinations thereof. In step 140 these interacted photons may be detected to thereby generate at least one near infrared data set representative of the sample. In one embodiment, this near infrared data set may comprise at least one of: a near infrared spectrum, a spatially accurate wavelength resolved near infrared image, and combinations thereof. In another embodiment, this near infrared data set may comprise a near infrared hyperspectral image. This data set may be analyzed in step 150 to thereby determine the presence or absence of a contaminant in the sample. In addition to detecting the presence or absence of a contaminant, the method of the present disclosure may also be configured so as to determine the approximate concentration of contaminant in a sample.

In one embodiment, the analyzing in step 150 may be achieved by comparing the near infrared data set to one or more reference data sets. These reference data sets may be located in a reference database and each reference data set may correspond to a known sample. In one embodiment, this comparing may be achieved by applying a chemometric technique. This technique may be any known in the art, including but not limited to: principal component analysis ("PCA"), multivariate curve resolution ("MCR"), partial least squares discriminant analysis ("PLSDA"), k means clustering, band t. entropy method, adaptive subspace detector, cosine correlation analysis ("CCA"), Euclidian distance analysis ("EDA"), partial least squares regression ("PLSR"), spectral mixture resolution ("SMR"), a spectral angle mapper metric, a spectral information divergence metric, a Mahalanobis distance metric, a spectral unmixing algorithm, and combinations thereof. A spectral unmixing metric is disclosed in U.S. Pat. No. 7,072,770 entitled "Method for Identifying Components of a Mixture via Spectral Analysis," which is hereby incorporated by reference in its entirety.

Figure 2:
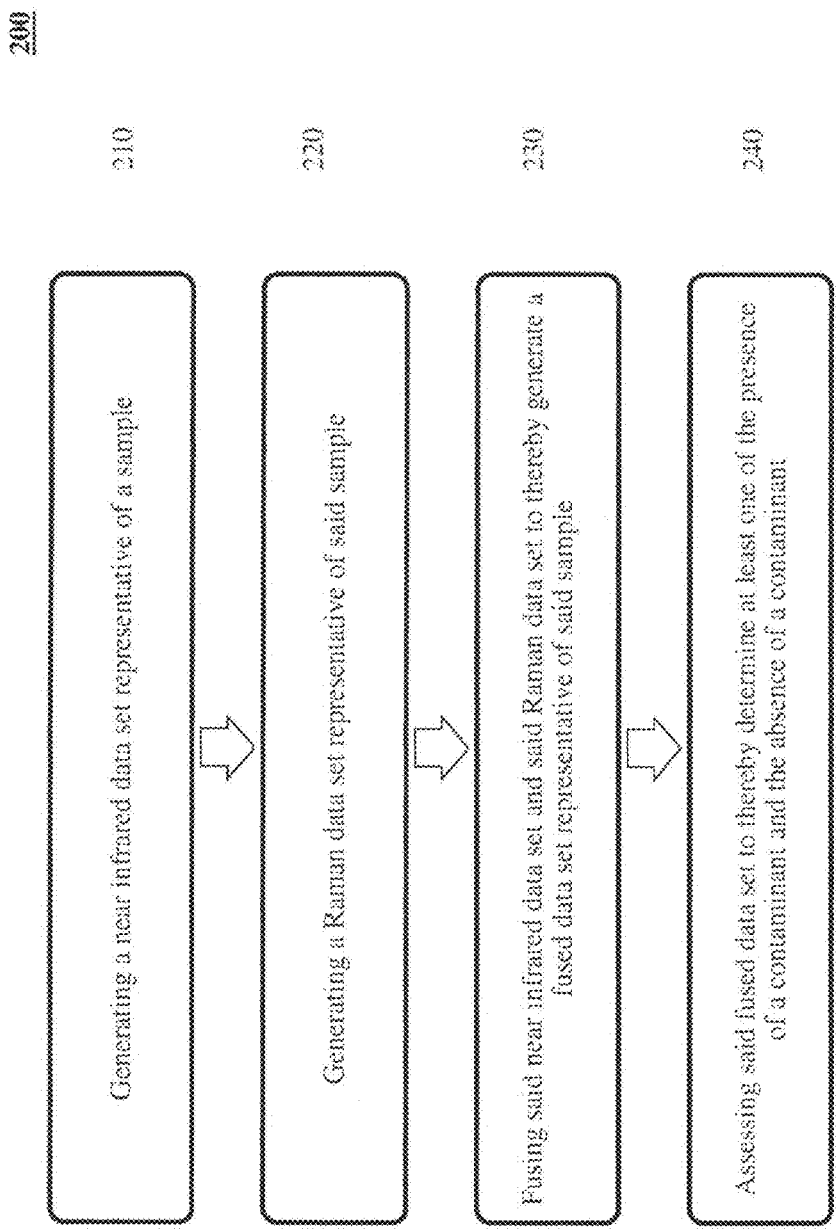
FIG. 2 is illustrative of one embodiment of a method of the present disclosure.

In another embodiment, the method 100 may further comprise fusing data generated using multiple modalities to thereby determine the presence or absence of a contaminant in a sample. In one embodiment, the near infrared data set may be fused with a brightfield image representative of the sample. In another embodiment, illustrated by FIG. 2, the near infrared data set may be fused with a Raman data set representative of the sample. In one embodiment, this Raman data set may comprise at least one of: a Raman spectrum, a spatially accurate wavelength resolved Raman image, and combinations thereof. In another embodiment, this Raman data set may comprise at least one hyperspectral Raman image. The method 200 may comprise generating a near infrared data set in step 210. A Raman data set may be generated in step 220. In step 230 this near infrared data set and the Raman data set may be fused to generate a fused data set representative of the sample. This fused data set may be assessed in step 240 to thereby determine at least one of the presence of a contaminant in a sample and the absence of a contaminant in a sample. This assessment may comprise comparing said fused data set with one or more reference data sets, corresponding to known samples. This comparison may be achieved by applying a chemometric technique or other method, such as Bayesian fusion. In addition, the use of intensity ratios at different wavelengths may be analyzed to further assess the spectral and hyperspectral data. The use of these intensity ratios may hold potential for reducing the influences from diverse samples; hence it could be universally applied for fast, accurate, specific, and routine screening of melamine contaminant in unknown products.

This Raman data set may be generated by illuminating the sample to thereby generate a second plurality of interacted photons. This illumination may comprise monochromatic light of an appropriate wavelength to thereby facilitate Raman scattering of photons interacted with the sample. These interacted photons may then be collected via at least one collection optics. These interacted photons may be passed through a tunable filter. This tunable filter may, in one embodiment, effectively separate the interacted photons into a plurality of predetermined wavelength bands. These interacted photons may then be detected to thereby generate a Raman data set representative of said sample.

Fusing a near infrared data set and a Raman data set representative of a sample may thereby generate a fused data set. In one embodiment, this fusion may be accomplished using fusion technology available from ChemImage Corporation, Pittsburgh, Pa. Such technology may comprise Forensic Integrated Search Technology ("FIST"), which is more fully described in the following U.S. patent applications, hereby incorporated by reference in their entireties: U.S. patent application Ser. No. 11/450,138, filed on Jun. 9, 2006, entitled "Forensic Integrated Search Technology"; U.S. patent application Ser. No. 12/017,445, filed on Jan. 22, 2008, entitled "Forensic Integrated Search Technology with Instrument Weight Factor Determination"; and U.S. patent application Ser. No. 12/339,805, filed on Dec. 19, 2008, entitled "Detection of Pathogenic Microorganisms Using Fused Sensor Data."

This fused data set may then be assessed to thereby determine the presence or absence of a contaminant in a sample. Such fusion holds potential for increasing the accuracy and reliability of sample analysis.

In one embodiment of the present disclosure, the use of different modalities may be used to first locate and area suspected of containing a contaminant and then interrogating this area of interest to determine whether or not the contaminant is in fact present. In one embodiment, brightfield imaging of a sample may be used to determine an area of interest. This area may then be interrogated using at least one of near infrared spectroscopy, near infrared imaging (including hyperspectral imaging), Raman spectroscopy, Raman imaging (including hyperspectral imaging), and combinations thereof. It may also be contemplated by the present disclosure to utilize near infrared methods to quickly scan a sample to locate an area of interest and then assess the sample using Raman methods. The present disclosure contemplates that any number of areas of interest may be located for inspection of a sample. Due to the nondestructive nature of the methods provided herein, multiple assessments may be made if necessary to confirm the presence or absence of a contaminant in a sample.

Figure 3:
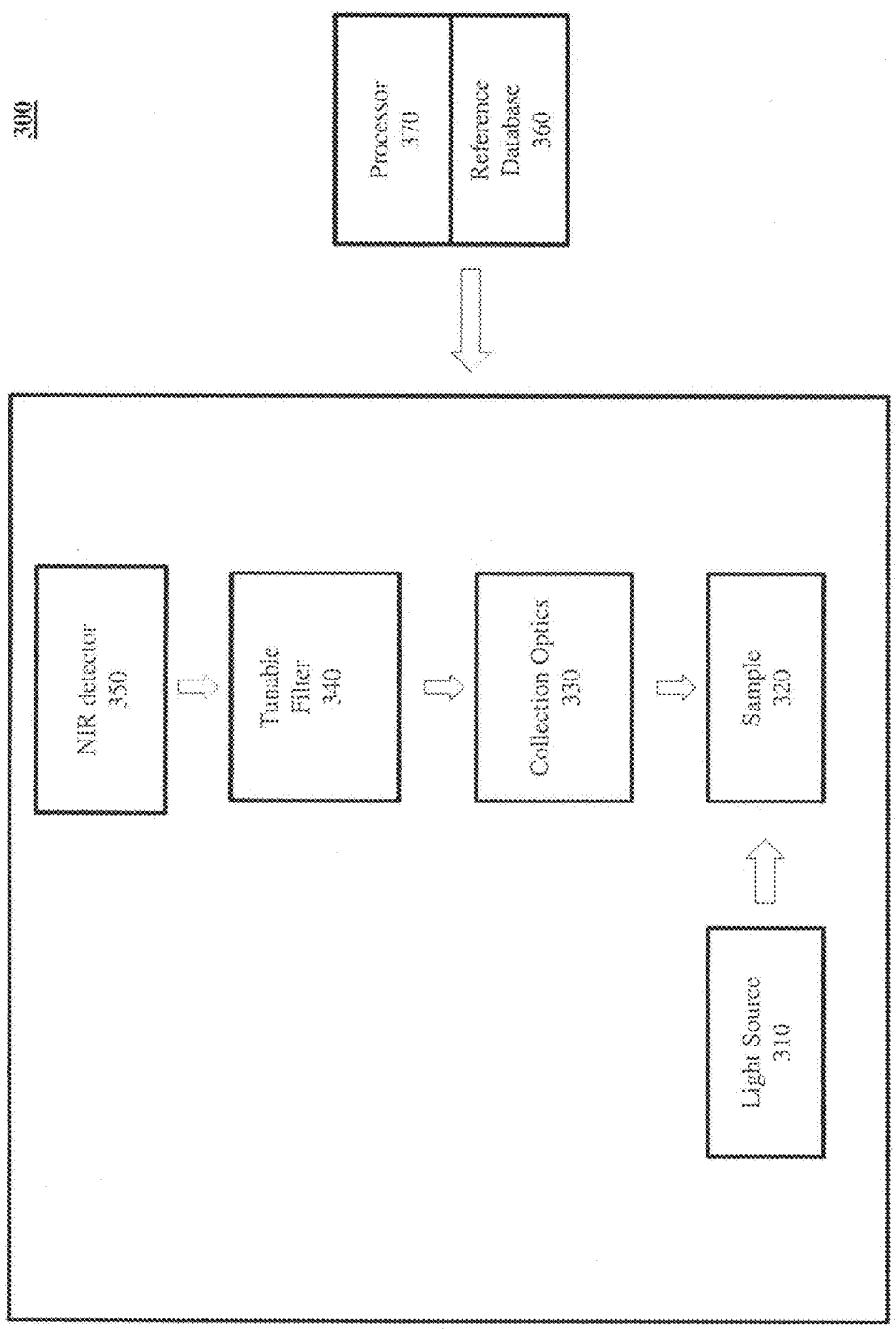
FIG. 3 is representative of one embodiment of a system of the present disclosure.

The present disclosure also provides for a system for detecting the presence of a contaminant in a sample. In one embodiment, illustrated by FIG. 3, the system 300 may comprise an illumination source 310 for illuminating a sample 320 to thereby generate a first plurality of interacted photons. These interacted photons may comprise photons scattered by the sample, photons emitted by the sample, photons reflected by the sample, photons absorbed by the sample, and combinations thereof. This first plurality of interacted photons may be collected by one or more collection optics 330. The interacted photons may then be passed through a tunable filter 340. This tunable filter 340 may be configured so as to sequentially filter said interacted photons into a plurality of predetermined wavelength bands. In one embodiment, this tunable filter 340 may comprise filter selected from the group consisting of: a multi-conjugate liquid crystal tunable filter, a liquid crystal tunable filter, and combinations thereof. In another embodiment, the tunable filter may comprise a filter selected from the group consisting of: an acusto-optical tunable filter ("AOTF"), Evans Split-Element liquid crystal tunable filter, Solc liquid crystal tunable filter, Ferroelectric liquid crystal tunable filter, Fabry Perot liquid crystal tunable filter, a hybrid filter, and combinations thereof. In one embodiment, this tunable filter 340 may comprise liquid crystal tunable filter technology available from ChemImage Corporation, Pittsburgh, Pa. This technology is more fully described in the following U.S. patents and pending U.S. patent applications, which are hereby incorporated by reference in their entireties: U.S. Pat. No. 6,992,809, issued on Jan. 31, 2006, entitled "Multi-Conjugate Liquid Crystal Tunable Filter"; U.S. Pat. No. 7,362,489, issued on Apr. 22, 2008, also entitled "Multi-Conjugate Liquid Crystal Tunable Filter"; U.S. Provisional Patent Application No. 61/324,963, filed on Apr. 16, 2010, entitled "Short-Wavelength Infrared (SWIR) Multi-Conjugate Liquid Crystal Tunable Filter"; U.S. Provisional Patent Application No. 61/460,816, filed on Jan. 7, 2011, entitled "Conformal Filter and Method for Use Thereof"; and U.S. Provisional Patent Application No. 61/403,141, filed on Sep. 10, 2010, entitled "Systems and Methods for Improving Imaging Technology."

The interacted photons may be detected at a near infrared detector 350. This detector 350 may be configured for generating a near infrared data set representative of a sample. In one embodiment, the near infrared detector 350 may be configured to generate at least one near infrared spectrum representative of the sample, a spatially accurate wavelength resolved near infrared image representative of the sample, and combinations thereof. In another embodiment, the near infrared detector 350 may be configured so as to generate at least one near infrared hyperspectral image representative of the sample. In another embodiment, the system may further comprise a second detector configured for generating a Raman data set representative of the sample.

In one embodiment, the system 300 may further comprise a reference database 360. This reference database 360 may comprise one or more reference data sets, wherein each reference data set corresponds to one or more known samples. The system may further comprise a processor 370 configured to compare at least one of the near infrared and Raman data sets to said reference data sets. This comparison may be achieved by applying a chemometric technique or other method including Bayesian fusion and/or FIST technology available from ChemImage Corporation, Pittsburgh, Pa.

The processor 370 may be configured to execute the machine readable program code so as to perform the methods of the present disclosure. In one embodiment, the program code may contain the ChemImage Xpert™ software available from ChemImage Corporation of Pittsburgh, Pa. The Xpert™ software may be used to process hyperspectral and spectroscopic data and information received from one or more detectors associated with the system 300 to obtain various spectral plots and images, and to also carry out various multivariate image analysis methods discussed herein.

Figure 4A:
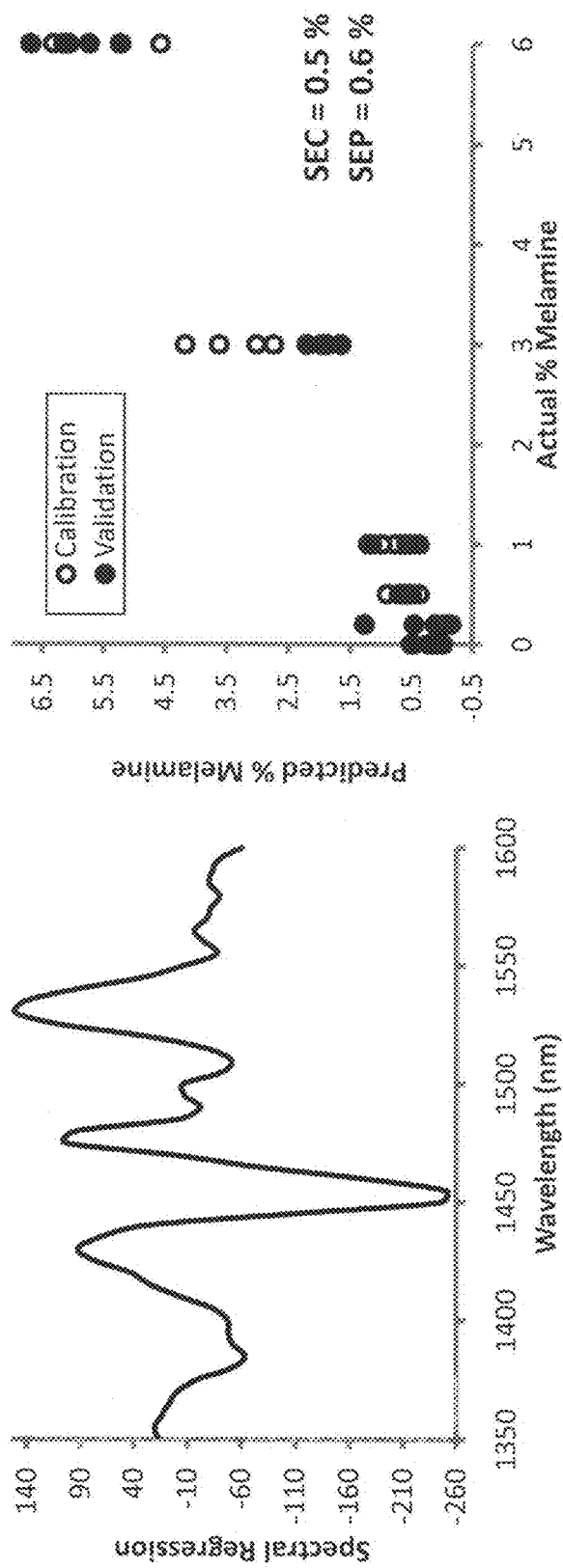
FIG. 4 is illustrative of detection capabilities using CONDOR™ technology.
Figure 4B:
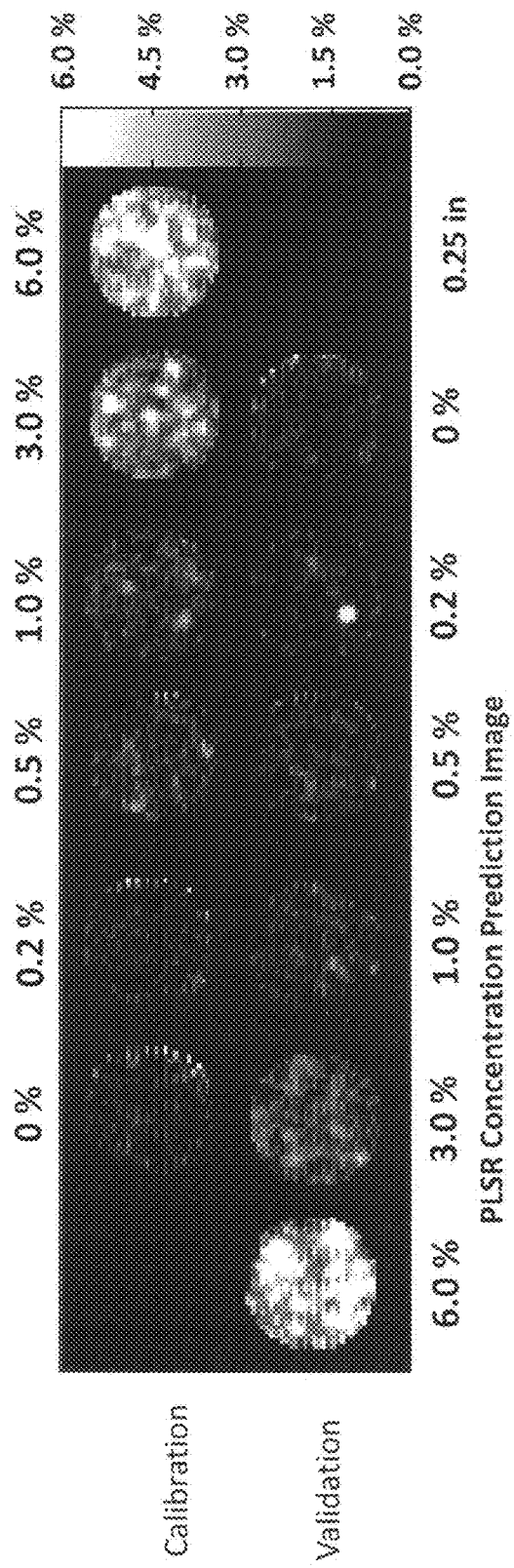
Figure 5:
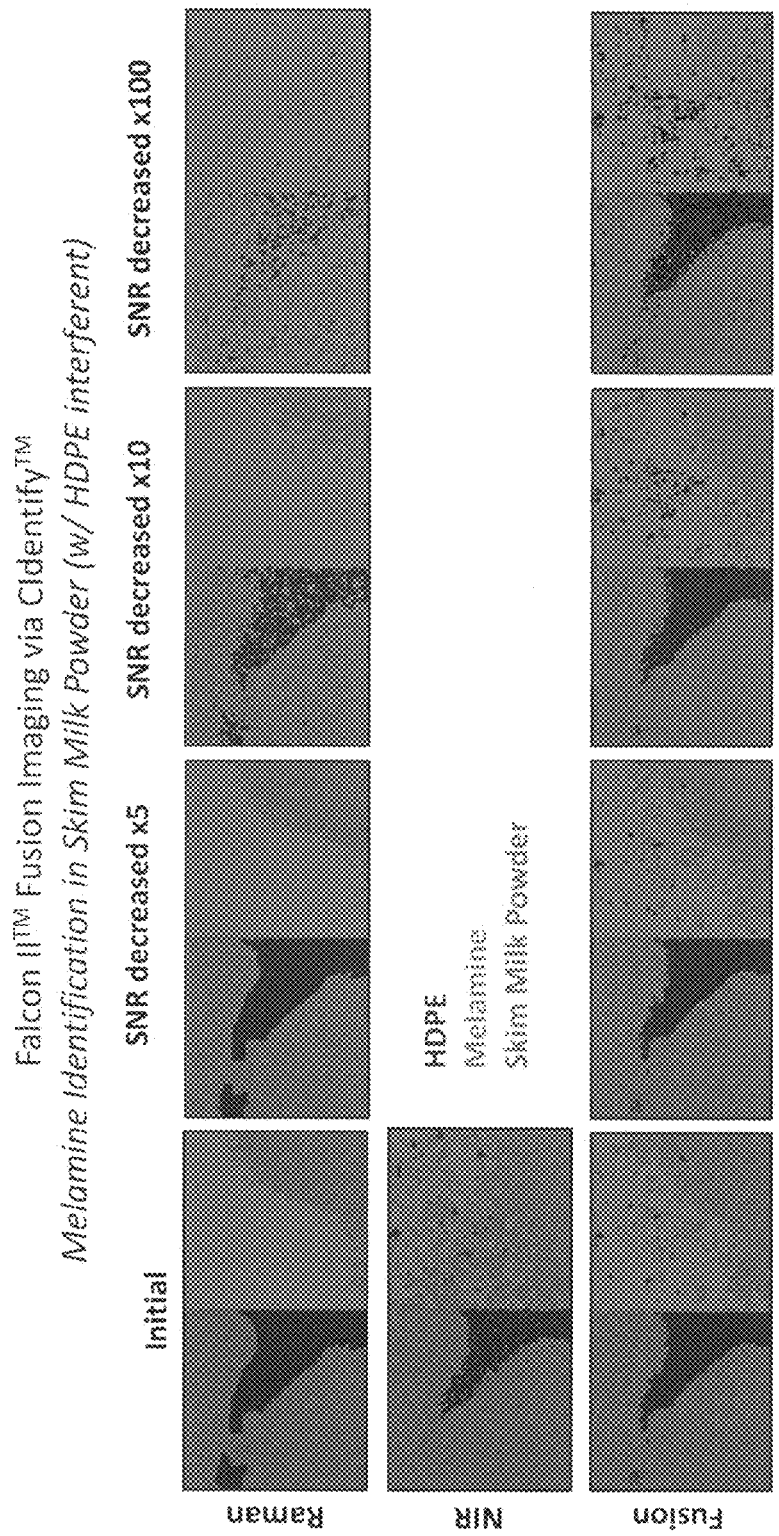
FIG. 5 is illustrative of fusion imaging using FALCON II™ instrumentation and CIdentify™.

FIGS. 4A, 4B, and 5 are provided to illustrate the detection capabilities of the present disclosure. FIG. 4A illustrates both calibration and validation acquired using CONDOR™ technology available from ChemImage Corporation, Pittsburgh, Pa. FIG. 4B illustrates a PLSR prediction image. In FIG. 4B, the first row represents calibration and the second row represents validation.

FIG. 5 illustrates the detection capabilities of the fusion methods described in the present disclosure. FIG. 5 illustrates melamine identification in skim milk powder (with HDPE interferent) using FALCON™ technology available from ChemImage Corporation, Pittsburgh, Pa. The Raman/NIR fusion result is closer to ground truth. Even as the Raman only classification degrades as SNR decreases, the fusion result maintains classification accuracy. Using NIR provides for fast acquisition time.

The present disclosure may be embodied in other specific forms without departing from the spirit or essential attributes of the disclosure. Accordingly, reference should be made to the appended claims, rather than the foregoing specification, as indicating the scope of the disclosure. Although the foregoing description is directed to the preferred embodiments of the disclosure, it is noted that other variations and modification will be apparent to those skilled in the art, and may be made without departing from the spirit or scope of the disclosure.

What is claimed is:
1. A method comprising:
 illuminating a sample to produce a first plurality of interacted photons;
 collecting the first plurality of interacted photons;
 passing the first plurality of interacted photons through a tunable filter to generate a first plurality and second plurality of filtered photons;
 detecting the first plurality of filtered photons to generate a near infrared data set representative of the first plurality of filtered photons;

detecting the second plurality of filtered photons to generate a Raman data set representative of the second plurality of filtered photons; and analyzing the near infrared data set and the Raman data set to determine one or more of the presence of a contaminant in the sample and the absence of a contaminant in the sample.

2. The method of claim 1, wherein the sample comprises at least one feed material.

3. The method of claim 2, wherein the feed material comprises one or more of wheat flour, corn gluten, soybean meal, and combinations thereof.

4. The method of claim 1, wherein the tunable filter comprises one or more of a multi-conjugate liquid crystal tunable filter, a liquid crystal tunable filter, and combinations thereof.

5. The method of claim 1, wherein the contaminant comprises one or more of melamine, cyanuric acid, ammeline, ammelide, and combinations thereof.

6. The method of claim 1, wherein the near infrared data set comprises one or more of a near infrared spectrum, a spatially accurate wavelength resolved near infrared image, and combinations thereof.

7. The method of claim 1, wherein the near infrared data set comprises at least one near infrared hyperspectral image.

8. The method of claim 1, wherein the analyzing comprises comparing the near infrared data set to a reference data set.

9. The method of claim 8, wherein the comparing comprises applying a chemometric technique.

10. The method of claim 1, further comprising fusing the near infrared data set with a brightfield image representative of the sample.

11. The method of claim 1, further comprising:
fusing the near infrared data set and the Raman data set to generate a fused data set; and
assessing the fused data set to determine one or more of the presence of a contaminant in a sample and the absence of a contaminant in a sample.

12. The method of claim 1, wherein the Raman data set comprises one or more of a Raman spectrum, a spatially accurate wavelength resolved Raman image, and combinations thereof.

13. The method of claim 1, wherein the Raman data set comprises at least one hyperspectral Raman image representative of the sample.

14. A system for determining the presence of a contaminant in a sample comprising:
an illumination source configured to illuminate a sample to generate a first plurality of interacted photons;
a collection optic configured to collect the first plurality of interacted photons;
a tunable filter configured to sequentially filter the first plurality of interacted photons and generate a first plurality and second plurality of filtered photons comprising a plurality of predetermined wavelength bands;
a first detector configured to detect the first plurality of filtered photons and generate at least one near infrared data set representative of the first plurality of filtered photons; and
a second detector configured to detect the second plurality of filtered photons and generate a Raman data set representative of the second plurality of filtered photons.

15. The system of claim 14, wherein the sample comprises at least one feed material.

16. The system of claim 14, wherein the contaminant comprises one or more of melamine, cyanuric acid, ammeline, ammelide, and combinations thereof.

17. The system of claim 14, wherein the tunable filter comprises one or more of a multi-conjugate liquid crystal tunable filter, a liquid crystal tunable filter, and combinations thereof.

18. The system of claim 14, wherein the near infrared data set comprises at least one near infrared hyperspectral image.

19. The system of claim 14, wherein the near infrared data set comprises one or more of a near infrared spectrum, a spatially accurate wavelength resolved near infrared image, and combinations thereof.

20. The system of claim 14, further comprising a reference database wherein the reference database comprises at least one reference data set associated with a known sample.

21. The system of claim 14, wherein the Raman data set comprises one or more of a Raman spectrum, a spatially accurate wavelength resolved Raman image, and combinations thereof.

22. A method comprising:
illuminating a sample to produce a first plurality of interacted photons;
collecting the first plurality of interacted photons;
passing the first plurality of interacted photons through a tunable filter to generate a first plurality and second plurality of filtered photons;
detecting the first plurality of filtered photons to generate a near infrared data set representative of the first plurality of filtered photons;
detecting the second plurality of filtered photons to generate a Raman data set representative of the second plurality of filtered photons;
fusing the near infrared data set and the Raman data set to generate a fused data set; and
analyzing the fused data set to determine one or more of the presence of a contaminant in the sample and the absence of a contaminant in the sample.

* * * * *